United States Patent
Köhler et al.

(10) Patent No.: US 8,836,504 B2
(45) Date of Patent: Sep. 16, 2014

(54) SYSTEM AND METHOD FOR THE REMOTE MONITORING OF POTTED PLANTS

(75) Inventors: Moritz Köhler, Zürich (CH); Philipp Bolliger, Winterthur (CH); Benedikt Ostermaier, Uster (CH)

(73) Assignee: Eidgenössische Technische Hochschule Zürich, Zürich (CH)

( * ) Notice: Subject to any disclaimer, the term of this patent is extended or adjusted under 35 U.S.C. 154(b) by 252 days.

(21) Appl. No.: 13/203,167

(22) PCT Filed: Feb. 24, 2010

(86) PCT No.: PCT/IB2010/000381
§ 371 (c)(1),
(2), (4) Date: Oct. 3, 2011

(87) PCT Pub. No.: WO2010/097689
PCT Pub. Date: Sep. 2, 2010

(65) Prior Publication Data
US 2012/0019382 A1 Jan. 26, 2012

(30) Foreign Application Priority Data
Feb. 25, 2009 (DE) .......... 10 2009 010 579

(51) Int. Cl.
*G08B 21/00* (2006.01)
*A01G 7/00* (2006.01)
(52) U.S. Cl.
CPC .................... *A01G 7/00* (2013.01)
USPC ................... 340/540; 340/500
(58) Field of Classification Search
USPC ........................................ 340/540
See application file for complete search history.

(56) References Cited

U.S. PATENT DOCUMENTS

| | | | | |
|---|---|---|---|---|
| 4,040,436 A | * | 8/1977 | Caldwell | 137/78.3 |
| 4,527,354 A | * | 7/1985 | Sellier | 47/81 |
| 6,700,395 B1 | * | 3/2004 | Perry | 324/696 |
| 6,701,665 B1 | * | 3/2004 | Ton et al. | 47/58.1 R |
| 7,400,975 B2 | | 7/2008 | Glenn et al. | |
| 7,439,867 B2 | * | 10/2008 | Staples | 340/602 |
| 7,660,698 B1 | * | 2/2010 | Seelig et al. | 702/170 |
| 8,009,048 B2 | * | 8/2011 | Hyde et al. | 340/572.1 |
| 2004/0088916 A1 | | 5/2004 | Ton et al. | |
| 2006/0108439 A1 | * | 5/2006 | Zur | 239/63 |
| 2007/0020851 A1 | | 1/2007 | Hong et al. | |
| 2007/0208511 A1 | | 9/2007 | Glenn et al. | |
| 2007/0208512 A1 | * | 9/2007 | Glenn et al. | 702/2 |
| 2007/0208591 A1 | | 9/2007 | Glenn et al. | |
| 2007/0208592 A1 | | 9/2007 | Glenn et al. | |
| 2010/0139160 A1 | * | 6/2010 | Hirsh et al. | 47/66.6 |

FOREIGN PATENT DOCUMENTS

| | | |
|---|---|---|
| DE | 10 2004 020 515 A1 | 11/2005 |
| DE | 10 2007 032 610 A1 | 1/2009 |
| EP | 0 846 440 A2 | 6/1998 |
| EP | 1 002 496 A1 | 5/2000 |
| EP | 1 352 606 A1 | 10/2003 |
| GB | 2 341 007 A | 3/2000 |
| GB | 2 426 908 A | 12/2006 |
| WO | 02/35193 A2 | 5/2002 |
| WO | 02/084248 A2 | 10/2002 |

OTHER PUBLICATIONS

International Preliminary Report on Patentability for corresponding International Application No. PCT/IB2010/000381 dated Aug. 30, 2011 (English translation.
German Search Report for corresponding German Application No. 10 2009 010 579.4 dated Mar. 3, 2009.
International Search Report for corresponding International Application No. PCT/IB2010/000381 mailed Jul. 27, 2010.

* cited by examiner

*Primary Examiner* — Kerri McNally
(74) *Attorney, Agent, or Firm* — Renner, Otto, Boisselle & Sklar, LLP

(57) ABSTRACT

The invention relates to a system and method for determining the state, state changes, and/or condition changes of a potted plant and for indicating the determined state of said object to the owner or user thereof, wherein the system and method locally determine at least one physical and/or chemical parameter on top of on the side of or in the immediate vicinity of the plant (1) to be monitored by means of preferably several sensors or sensing elements (3). Said physical and/or chemical parameter is processed into a coded digital parameter signal and transmitted wirelessly, optionally by means of intermediate stages, to a central processor, which determines a statement about the state of the plant (1) from said coded digital parameter signal and other digital as an optical and/or acoustic indication of the current or prognosticated state of the plant/object (1). The sensation of the object is preferably simulated, which aims at triggering emotions in the user himself, for example, by means of language- and culture-independent icons. The data are determined, processed, and transmitted without significant time delay, in other words, in real time in principle. In the central processing, the data can be combined with further information, for example, the requirements profile of the object, historical data, data of similar objects, climate data, or weather forecasts. The user of the system can automatically be contacted if certain events are ascertained for the monitored object, if for example, an unfavorable forecast or a harmful parameter is ascertained. The sensors or sensing elements and further components are preferably placed in a plant container, an "intelligent flowerpot" so to speak, in such a way that the sensors or sensing elements are undetectable or barely detectable. Said "intelligent flowerpot" can comprise a "mobile sensor clip" as an essential component in addition to sensors arranged therein or thereon.

20 Claims, 15 Drawing Sheets

Figure 2A:
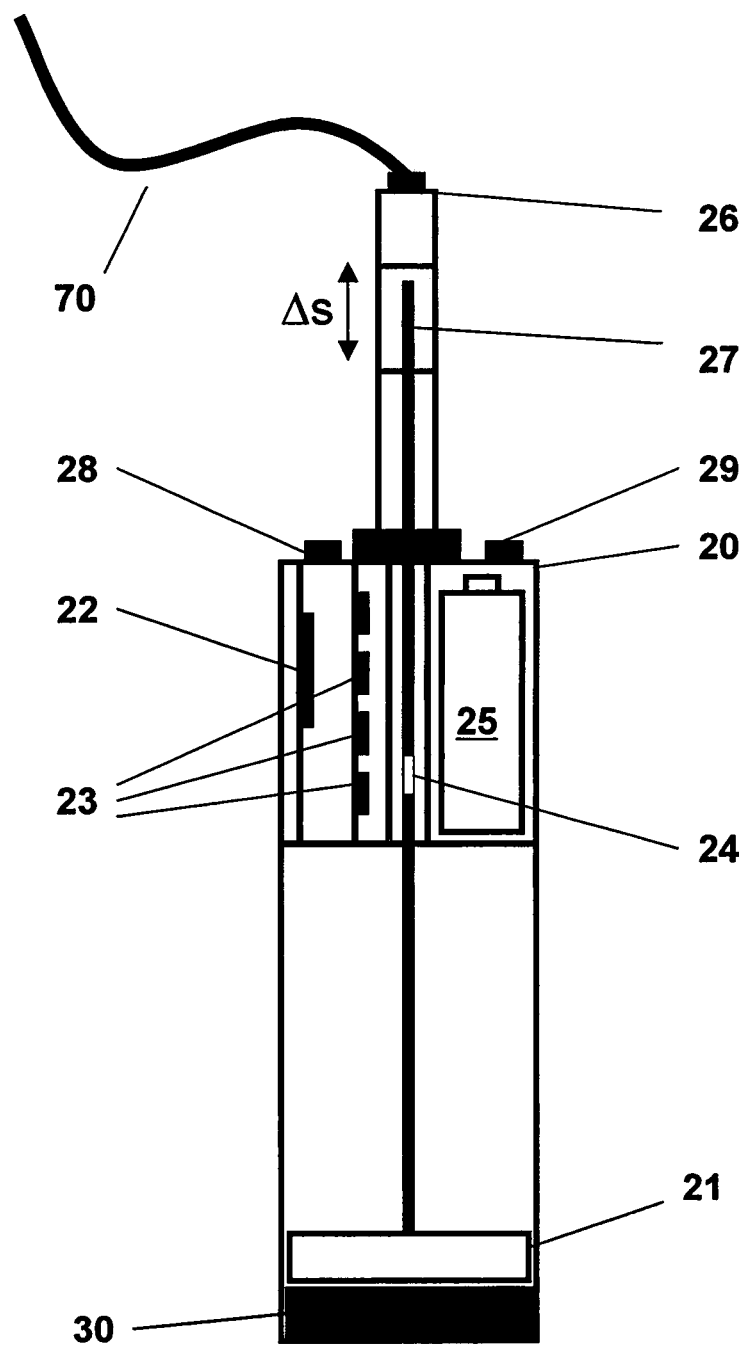

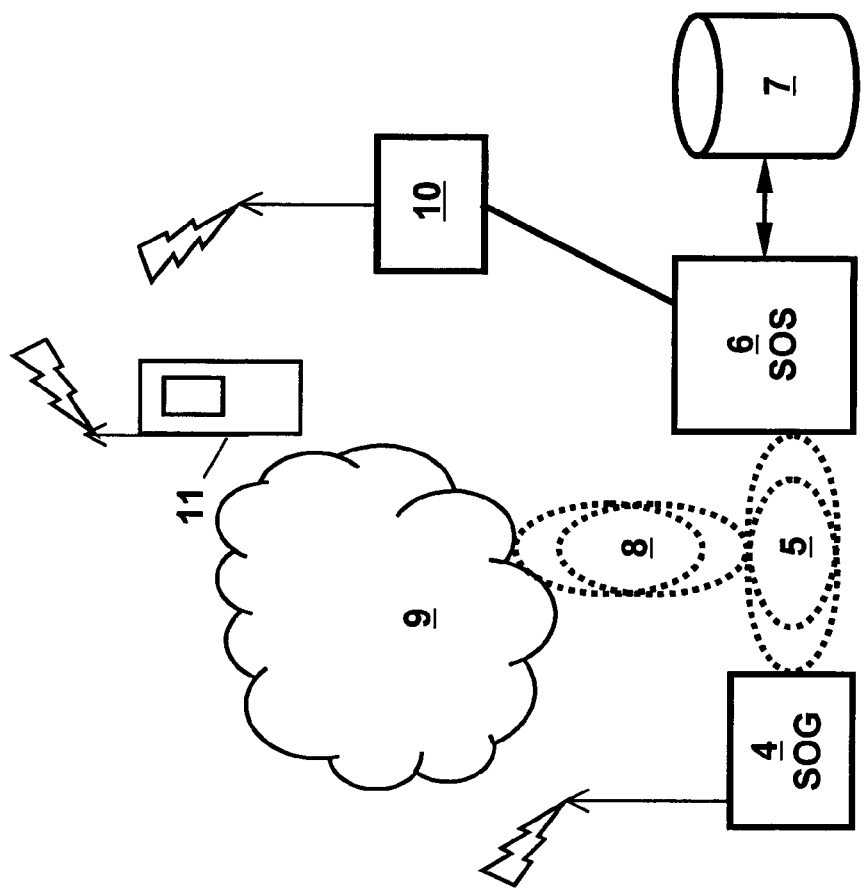
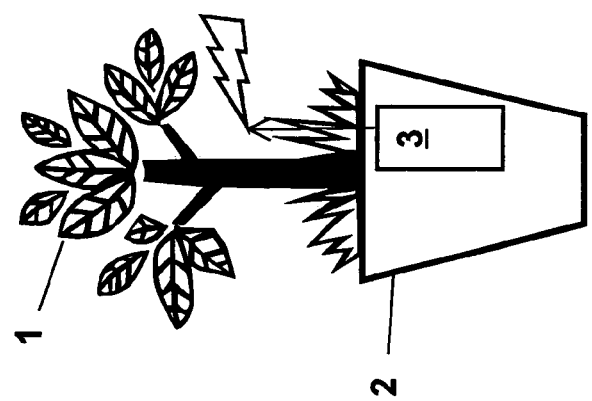
Fig. 1

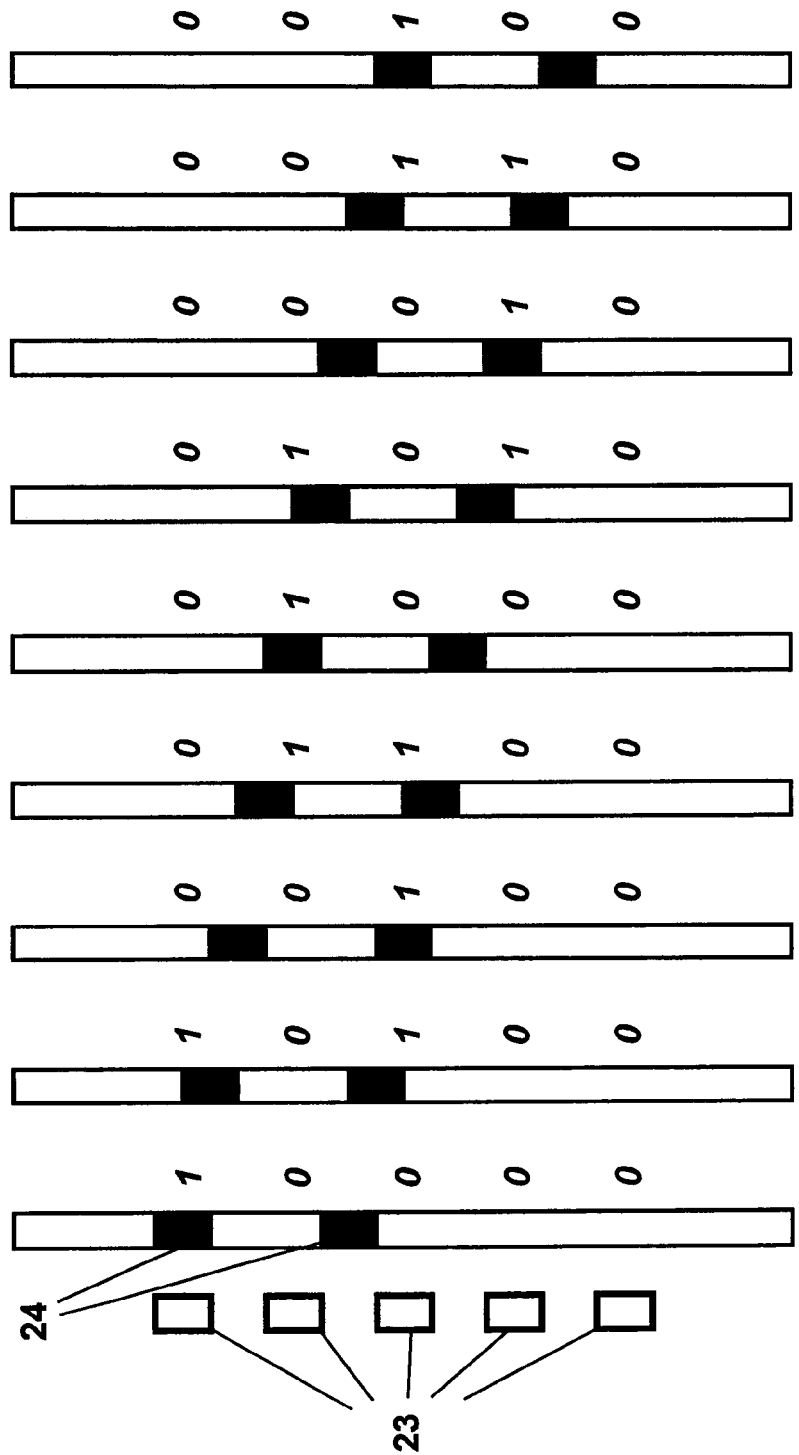

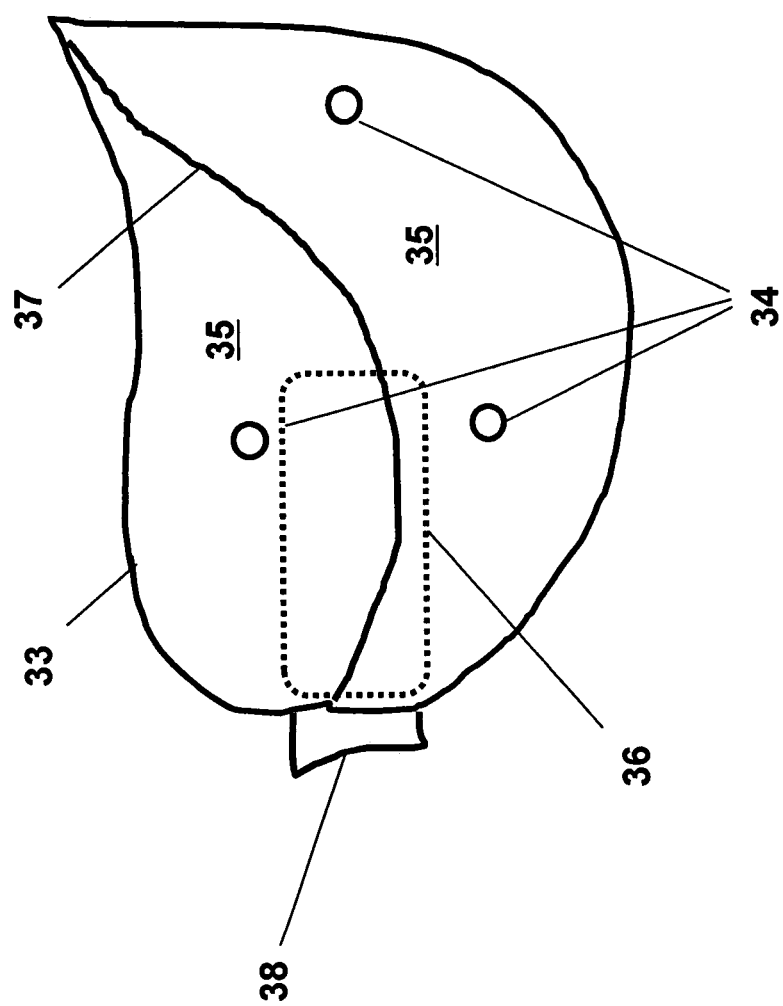

SYSTEM AND METHOD FOR THE REMOTE MONITORING OF POTTED PLANTS

FIELD OF TECHNOLOGY

The present invention relates to the automatic monitoring, measuring, checking or inspection and corresponding display or indication of values determined, or values determined therefrom, which are of significance for the care and the "well-being" of plants. The system according to the invention and suitable for this purpose and the method carried out thereby permits informing the user or owner of the particular state or the condition of a plant independent of location in easily remembered and immediately understandable form. Herein to the user of the system the current or predicted state of a plant is conveyed in a manner which simulates the emotions of the plant with the aim of triggering emotions in the user himself, for example by using language- and culture-independent icons. The user can furthermore be immediately notified through the system according to the invention as soon as one of the monitored plants is at risk of being harmed. The system comprises one or more plant containers, into which in the least conspicuous manner sensors and additional components are integrated, which determine several parameters, preferably in real time, for example temperature, light incidence, air humidity and/or soil moisture or the nutrient or harmful substance content. Across a local network these parameters are supplied, preferably wirelessly, as digitized data for example via a gateway, a hub or a connection to a mobile radio network, to a central office or a central server. The major portion of data processing is carried out here. The resulting variables of state for the particular plants are preferably wirelessly transmitted to a receiver, for example a mobile device, PDA, cell phone or PC and indicated to the user in as simple a manner as possible yet memorable representation, for example through language or culture independent icons.

BACKGROUND AND PRIOR ART

An important problem in the care of plants is their time-delayed reaction to external effects. Even if it is detected that one plant is not optimally cared for, it is often difficult to determine the concrete causes. Added to this is that even a one-time brief event, such as for example a forgotten open window in the winter, can have permanent negative effects on a plant.

The listed problems have led to a number of partial solutions. Some of them are described in the following.

The published US application 2007/0208511 shows the architecture of a computerized plant monitoring system in which the user must classify the plant, however he must do so manually. A sensing element provided with a storage means is inserted into the soil for some length of time, subsequently removed and connected to a computer that reads out the measured and stored data. A corresponding computer program subsequently determines the state of the plant and indicates this state to the user. One disadvantage of this system consists in that no real time observation is possible but only the values of the past can be evaluated. In addition, it appears difficult to utilize the system for plants which must be watered from below. Furthermore, the sensing element is visible since it must be inserted into the soil and be removed again to read it out.

The published US application 2007/0208512 discloses a plant monitoring system that operates in real time and also comprises a sensing element and a computer. The sensing element, again, includes storage means. The profile of the plant is entered into this storage by the computer and the sensing element is placed in the proximity of the plant. As soon as adverse conditions are detected in the vicinity of the plant that could negatively impact the plant, the sensing element will indicate this. Here also sensing element and computer are not connected in real time but the sensing element is connected in advance to the computer in order to store the profile data of the plant. A change of the profile data since their last storage therefore has no effect on the indication of the sensing element.

In the published US application 2007/0208591 a system is described in which a computer is utilized in order to compare vicinity data with stored plant profiles. This is intended to determine which plants are suitable for the selected placement site. The user receives herein directly commercial information for the purchase of such plants.

In the published US application 2007/0208592 a similar computerized selection system is described in which at the site at which a plant is to be placed, a measuring means is installed which records and stores the vicinity data for a certain length of time. The measuring means is subsequently removed, the measured data are transmitted to a computer, analyzed and suggestions are made regarding plants that are suitable for this location.

U.S. Pat. No. 7,400,975 describes a sensing element with a storage which can be applied in an architecture such as in the above US application 2007/020851. The described sensing element is comprised of two parts. A lower part houses a number of sensors disposed in the ground. The upper part is a detachable communication interface which stores the determined data. The communication interface is manually separated from the sensing element and connected to a computer and can thus transmit to it the stored data. This also does not involve a real time representation.

In the publication DE 10 2007 032 610 a method is proposed for the remote monitoring of the medical status of a user. The data acquisition is performed through sensors applied on the body of the user, which sensors issue data across a multistage data processing system, for example a physician or the user himself. In this publication neither sensors of the type described in this application nor measurements of temperature, humidity/moisture, harmful substance content, etc. are provided in the vicinity of a plant.

Publication EP 0 846 440 involves the monitoring of the physiological status of persons, in particular soldiers. Here the data acquisition also takes place through sensors applied on the body of the soldier and a GPS. Similar to the preceding publication, what is involved here is not the vicinity of a plant but rather measuring in the vicinity of a person.

Publication EP 1 352 606 also involves monitoring physiological data of a patient. Of interest here is that a number of basic data are entered in advance and that limit values are provided. When these limit values are exceeded an alarm report is issued. However, here also monitoring plants is not involved whereby the present application is differentiated.

In the laid open application DE 10 2004 020 515 the remote monitoring of muscle activities in humans and animals is described. The measuring instrument proper is herein separate from the data processing. A small battery-operated device is attached on a patient or animal, which device wirelessly transmits the determined measured values. The differentiation against this publication is again that no reference to plants is made therein.

European patent EP 1 002 496 also involves continuously monitoring and analyzing the physiological functions of a patient. This application deals especially with the wireless remote monitoring of the determined measurement values, which is carried out by means of different radio networks. Neither the communication of the measuring transducer/sensors with each other nor the reference to the vicinity of a plant are disclosed.

Application US 2004/0 088 916 involves a plant monitoring system with a number of sensors which transfer the determined data via radio. However, this system is more directed toward monitoring a commercial cultivation area and does not describe any details such as are contained in the claims of the present application. The present application is hereby differentiated against the above described US application.

Inherent in these offered partial solutions are diverse disadvantages. One disadvantage is the time delay between the detection of adverse conditions and the notification of the owner or user, if such notification is provided at all. Another disadvantage is the impairment of the appearance of the plant if, for example, the sensing elements are visible in the proximity of the plant. It is also cumbersome if a sensing element must be removed in order to read out the data and, in most cases, must also be cleaned before it can be connected to the computer. In addition, the latter requires the presence of the owner or user Inherent in the introduced systems which relate to remote monitoring of persons is accordingly that they do not refer to the monitoring of plants in buildings or in the immediate proximity of a building Inherent in the introduced systems, which relate to the remote monitoring of plants, is that they are either not suitable for remote monitoring or are exclusively for application in commercial cultivation areas. In the second case, there is accordingly no solution for sensors that are too large and disturbing in or on a flower pot.

A further disadvantage of the described systems lies in that each case represents only a partial solution. Stated differently, no fusion of the determined data takes place. However, the entire picture of the state of a plant can only be obtained if all determined data are entered into the depiction of this picture.

THE INVENTION

Building on this prior art, the invention addresses the problem of providing an integrated system which permits the remote monitoring of a plant, wherein the owner or user can be notified in a timely manner and directly in a simple manner as soon as adverse circumstances call into question the thriving or the health of a plant. This notification should also be possible if the owner or user is not in the vicinity of the object. Extrapolated data, e.g. prognoses regarding future sensor values (based inter alia on historical values, plant type, placement location, season of the year, weather report, etc.) can also be taken into account. The plant in some cases can draw attention to itself in a timely manner should a problem become apparent. An example of such notification is the message: "need water within 2 days!". This message informs the user before damage occurs. In order for the owner to be able to receive and view or hear the notification he should also not need to carry on his person any special devices. The invention can also be realized such that instructions or advice are provided to the owner or user as to how he can influence the thriving and the health of the object. An essential aspect of the invention is the integration of the technical components into the container of the plant in order not to impair its appearance and esthetics through the monitoring of the plant. Furthermore, the system is to be simple to handle, e.g. an owner or user must be able to deal effortlessly therewith without needing to have special computer knowledge.

In order to achieve the described functionality the particular parameters of the state of the plant are inconspicuously measured in real time, are transmitted, analyzed and a message or corresponding signal is conveyed to the owner or user in the form of a message.

The system and method according to the invention for determining and indicating the state and changes of state and condition of a plant to an owner or user, is distinguished in that sensing elements are disposed on, at or in the immediate proximity of a plant container, which determine at least one physical parameter locally. Together with other components, these sensing elements are integrated into the plant container and the permit coding of the parameter signal and its wireless transmission to a receiver. This receiver is connected to a processor which processes the received parameter signals, the generated output signal representing a statement about the state of the object. The generated output signal (for example state of health, location, temperature) is subsequently wirelessly transmitted to a, preferably, mobile indicator device which conveys to the owner or user a visual or audible notification regarding the state of the plant.

Herein, at least one, preferably several, of the following physical parameters are determined and analyzed:

Temperature and/or moisture of the soil,
Temperature and/or level of the water column of the nutrient solution,
Temperature and/or humidity of the ambient air,
Nutrient or harmful substance content of the soil or of the nutrient solution,
Length and/or intensity and/or type (polarization, light color and temperature) of the light incident on the plant.

As described in the description of the invention in the next section, an intelligent flower pot represents an essential part of the invention. By "intelligent flower pot" is here to be understood a flower pot, which has been expanded by sensors that can measure one or several of the above listed physical parameters. An intelligent flower pot, moreover, comprises a processor and storage means in order to be able to process the signals of the sensors. This intelligent flower pot can optionally transmit directly, or with the aid of a relay station, the sensor data across a wireless communication module to the Internet where further processing of the data takes place.

Details of the system and method according to the invention can be found in the following description and the patent claims.

DESCRIPTION OF SEVERAL EMBODIMENTS EXAMPLES

Figures 4A, 4B:
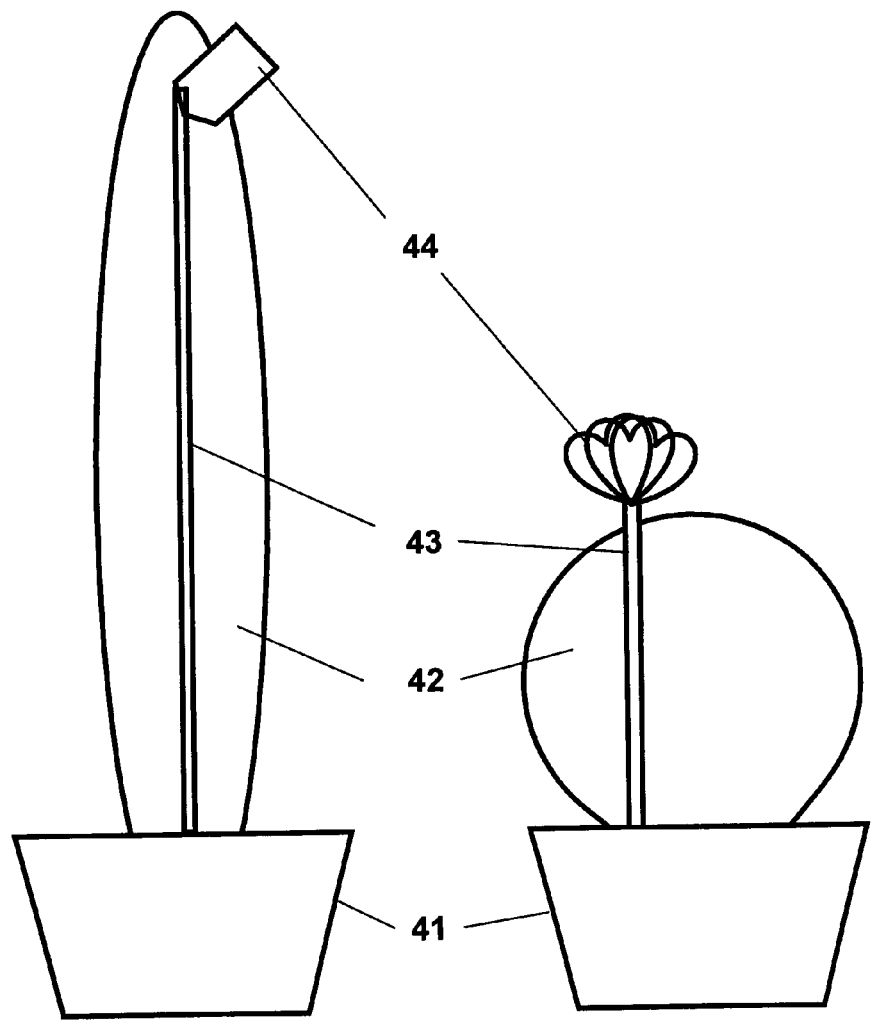
Figure 5A:
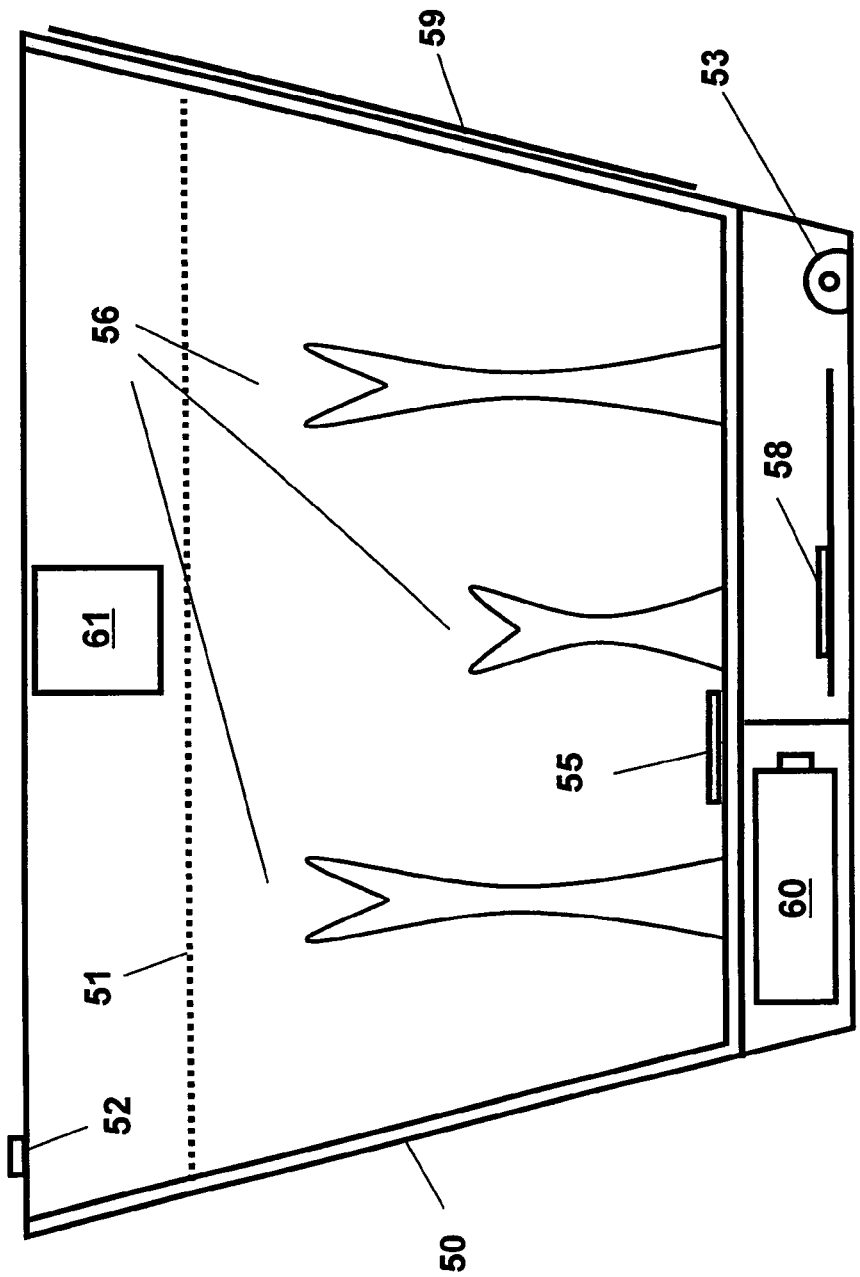
Figure 5B:
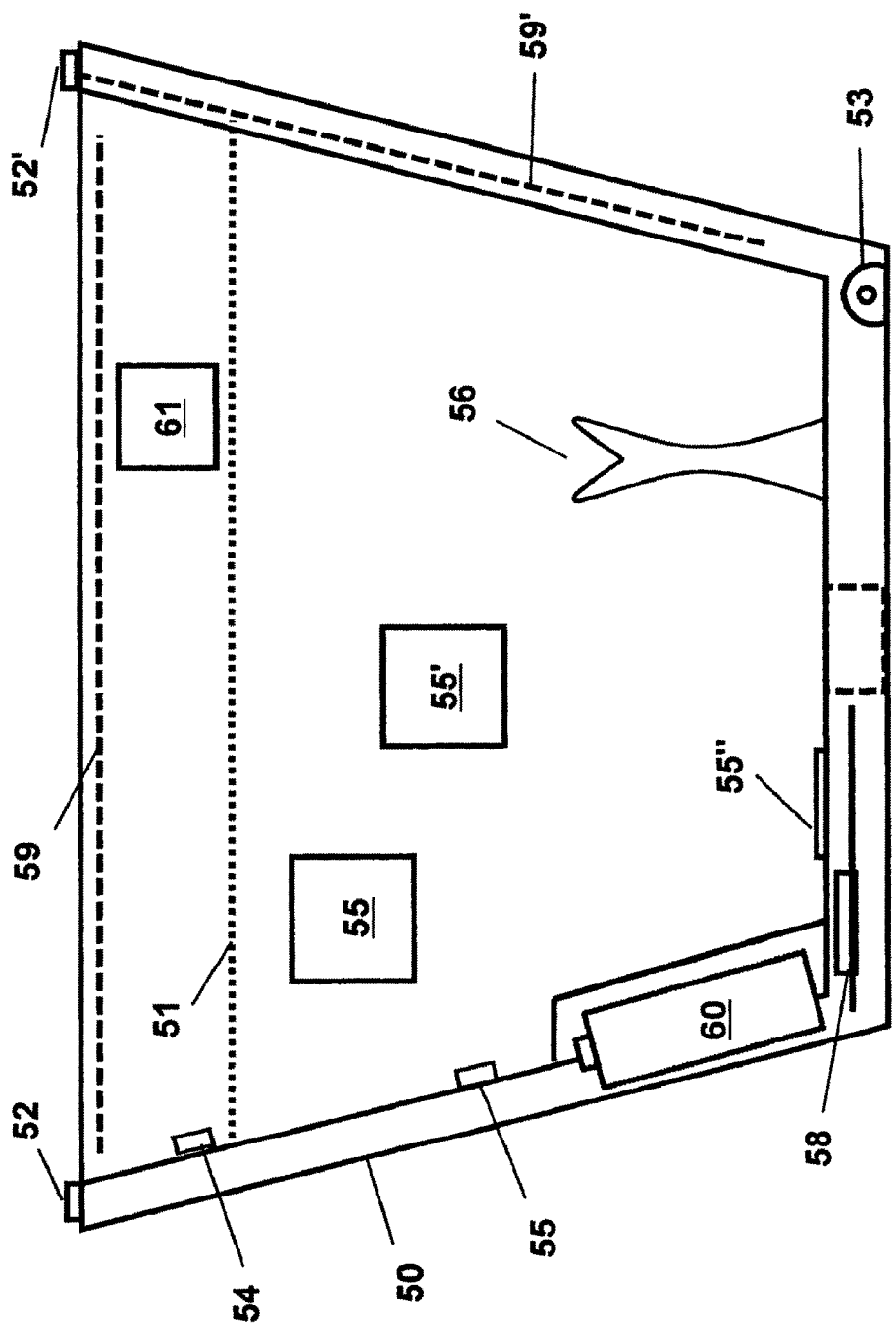
Figure 5C:
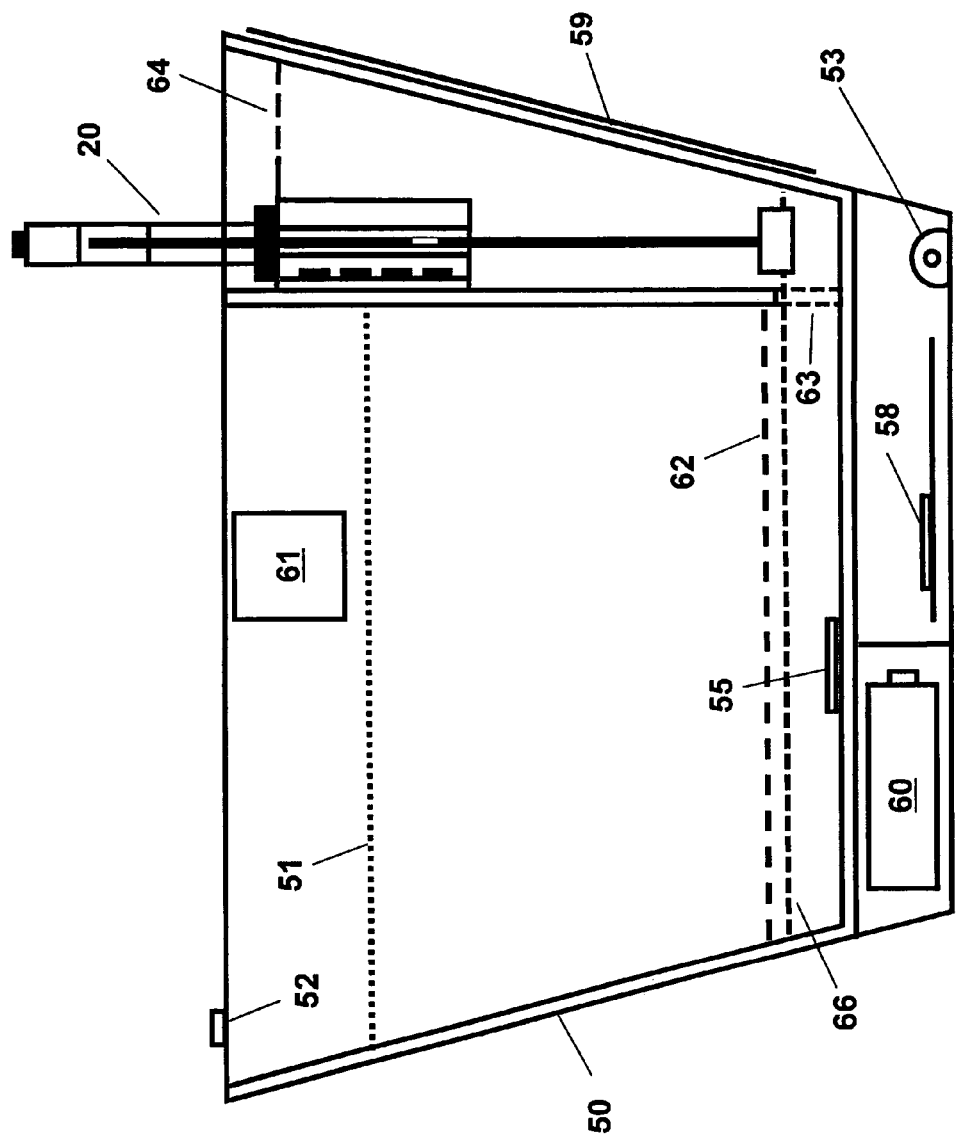
Figure 5D:
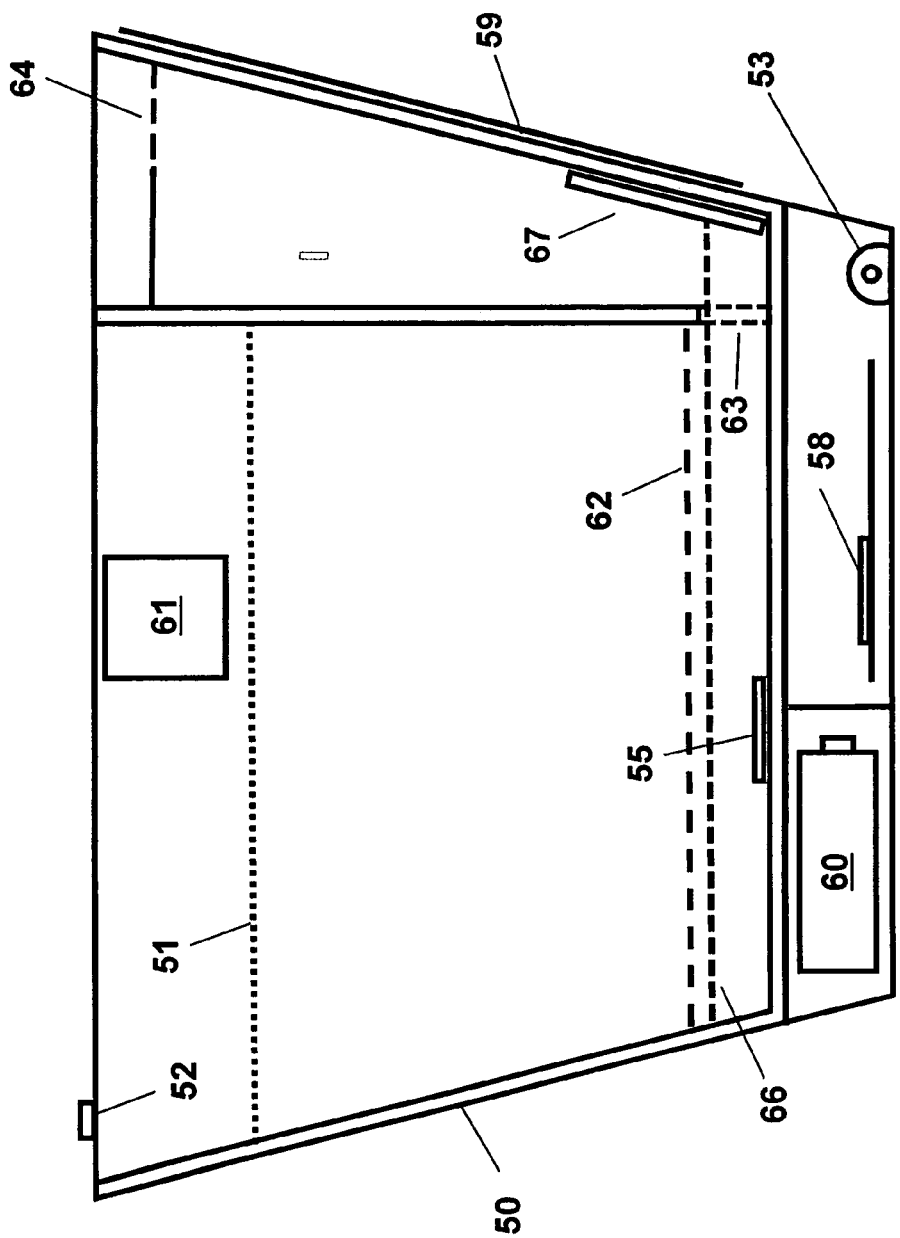
Figure 5E:
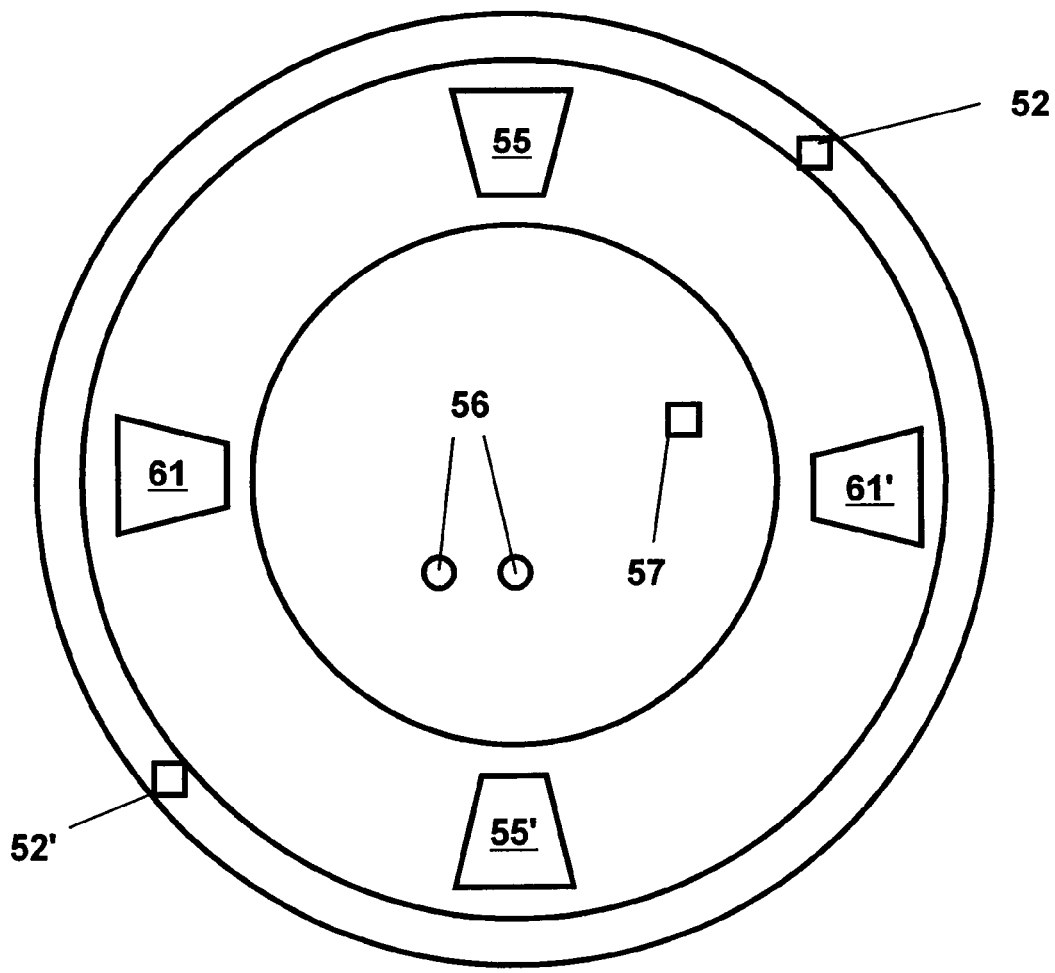
Figure 6A:
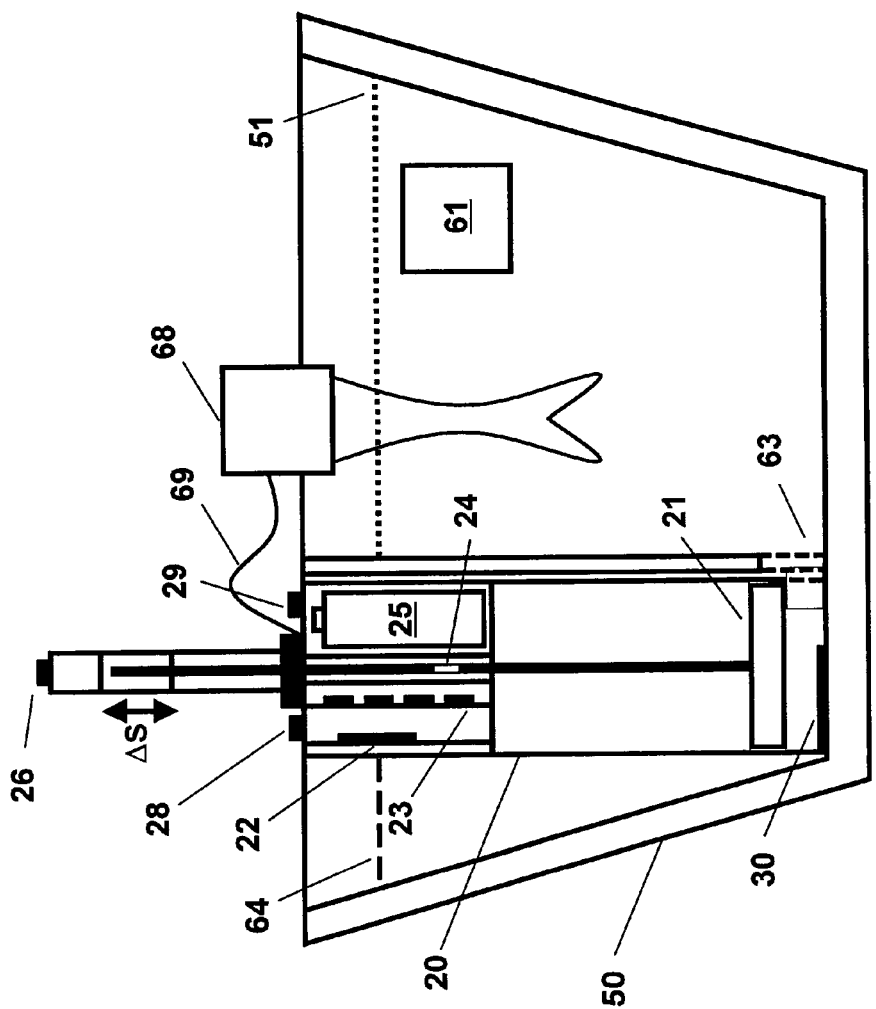
Figure 6B:
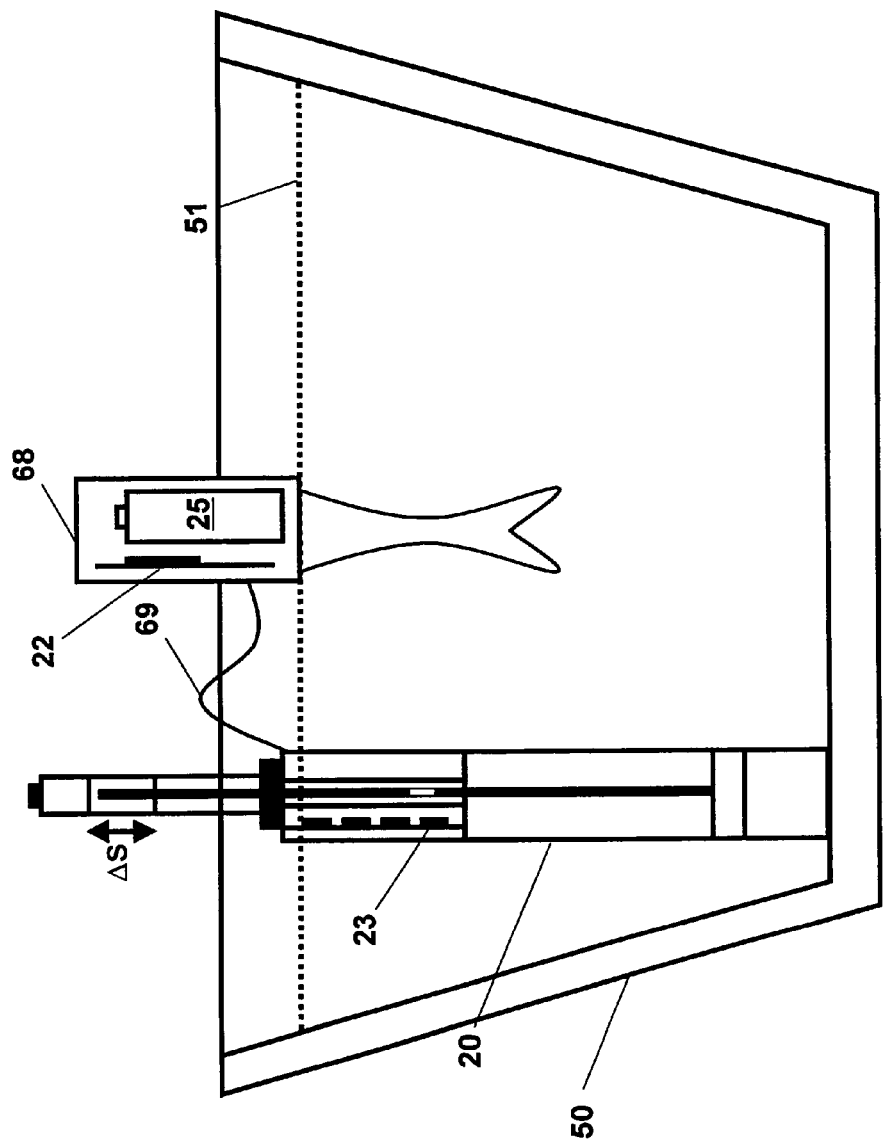

In the following the invention will be described in detail in conjunction with some embodiment examples which are also shown in the associated drawing. Depicted in the drawings are:

FIG. 1 an overview over the entire system,
FIGS. 2*a*-2*e* partial implementation of the intelligent flower pot,
FIG. 3 example of an inconspicuous so-called sensor clip,
FIGS. 4*a*-4*b* examples of sensor clip dispositions,
FIGS. 5*a*-5*e* examples of intelligent flower pots, and
FIGS. 6*a*-6*b* examples of a realization of an intelligent flower pot comprised of sensors inserted into the substrate.

FIG. 1 shows by example an overview over the entire system. A plant 1 is located in a flower pot 2, that is filled with a substrate or soil, swelling clay or an hors-sol material, such as coconut fibers or rock wool. In the following description and in the patent claims, "soil" is to be understood as any material in which plants can root or grow, thus, for example, also swelling clay or an hors-sol material.

In the flower pot is also shown a sensor 3, which, for example, measures the water level. As described below, not only a single sensor or sensor node is utilized, but rather at least two sensors for the various parameter measurements will be located in or on the flower pot.

It is understood that the parameter signals could also be transmitted directly from the flower pot 2 to the Internet 5. For this purpose the flower pot 2 requires a transmitting/receiving unit, which conforms to the standard of an already defined infranet structure, here being considered, for example, GSM, UMTS or IEEE 802.11. However, these standards were developed for high data transmission rates (UMTS, IEEE 802.11) or mobile data transmission (UMTS, GSM). The price for this functionality, as a rule, is a very much higher energy consumption of the transmitter. In the present case, however, only low data quantities are transmitted and the end devices are stationary. Therefore, energy saving standards can be applied, for example Zigbee, Z-wave or 6LoWPAN/802.15.4. For these standards, there are, however, no ubiquitous infrastructures, e.g. it is necessary to build an infrastructure on site. The optional Smart Object Gateway (SOG) 4 serves precisely for this purpose. Transmission across an available yet high energy consumption infrastructure (for example GSM, UMTS or IEEE 802.11) can make sense if the number of data transmission processes is low. For example, it is entirely sensible to draw on a high energy consumption standard if data are only transmitted once a day.

It should be noted however, that the SOG 4 can draw on an already available wireless infrastructure in order to transfer data to the Internet 5. It is understood, that the SOG in particular can also be, for example, a GSM, UMTS or IEEE 802.11 access point, which means that the SOG can be a part of an independent telecommunication infrastructure. It consequently functions as a gateway between an energy-efficient and a less energy efficient transmission technology.

The digital output signals output by the intelligent flower pot(s) 2, which represent said parameters, are optionally transmitted across the described gateway SOG 4 to a central computer or server 6.

This central computer or server is here denoted as a Smart Object Server (SOS) 6. Here central data processing occurs, wherein existing data stored in a storage 7 can be accessed. The SOS 6 can furthermore also access external data sources 9, which takes place across the Internet connection 8. Therewith it becomes feasible to determine the precise status of the observed plant 1, to detect faulty developments and feasibilities for their rectification and to assess possible risks, in short to create a comprehensive overall picture of the observed object 1.

The setup comprising an intelligent flower pot that wirelessly transfers data either directly or across a Smart Object Gateway to a Smart Object Server is assumed to be a known standard method. The intelligent flower pot is embedded in this larger architecture.

The overall picture of the monitored plant is conveyed to the owner or user of the plant. This can also take place via the Internet to which the SOS 6 is already connected. (This feasibility is not depicted in FIG. 1). A more elegant method consists in utilizing a mobile end device, which includes a wireless network interface (such as, for example, a mobile telephone or Smartphone) as that user interface and to indicate to the owner in an obvious manner the state of his plant (or a large number of his plants). An automatic notification of the user or owner can be provided, for example in the event of lack of water of the plant and therewith the risk of withering, or also a query started by the owner to the system regarding the state or condition of the plant. The depiction of the particular state or the condition of a plant is carried out in easily remembered, immediately comprehensible form. To this end the current or predicted state of the plant is conveyed to the user of the system in a manner which simulates the emotions of the plant and therefore is intended to trigger emotions in the user himself, for example through language- and culture-independent icons.

Both of these processes take place across a telecommunication network which preferably supports the Internet protocol, in particular the mobile radio network, for example according to the GSM or UMTS standard. For this purpose the SOS 6 is connected to one or also several mobile radio provider(s) 10 from whose location the connection across the mobile radio network with the mobile radio device 12 of the user or owner of the plant 1 is established. Control of the content of this communication takes place primarily through the SOS 6.

The function of the system according to the invention will be explained with reference to the following examples.

Example 1

The user or owner of the system wishes to obtain information regarding the vitality of one of his plants while he is on vacation. For this purpose he starts an application on his mobile telephone 11 which sets up a connection with the SOS 6. Since the smart flower pot in which the plant is located sends measured values to the SOS 6 during the entire time, it is now feasible to calculate here, based on current and historic data as well as through the comparison of other like plants, a detailed report of its condition. This condition is now sent to the mobile telephone of the user 11 indicated, for example, since the plant is well, by a laughing smiley.

Example 2

After installation, there is a logic link between a user, a flower pot and the plant, which is located in the particular pot. At regular intervals or upon the occurrence of an extraordinary event, the flower pot transfers sensor values to the SOS 6. This can readily be explained using lack of water as an example. Since the water level of the plant changes only extremely slowly, it suffices to transfer the water level, for example, once daily. It is understood that the water level, if needed, can also be measured using a higher or lower sampling rate. The user is at any time in the position to query the current water level since the communication takes place between his mobile telephone and the SOS 6. If the water level falls below a tolerance mark, an alarm is generated and the user receives a message on his mobile telephone. If the user now waters the corresponding plant, the system makes the water level visible on the mobile telephone in real time. A rising water level is thereby interpreted as an extraordinary event since, after all, a watering process is carried out in only a fraction of the overall system time. The data are therefore not transferred at regular intervals but rather only when exceeding a tolerance range. In the case of the water level this range would be very small with the result that even only minor changes are interpreted as an extraordinary event. This event, in turn, initiates a message through the message chain 'sensor node/SOG/SOS/and lastly the mobile telephone.' The message can be transferred so fast that for the user tracing back his own activity, thus of watering, is made possible in real time.

As already explained above, the core of the invention lies in the least conspicuous measuring of parameters through sensors and their wireless transfer. This information is conveyed to the user or owner of the object virtually in real time. In the depicted system the following parameters are measured:
Temperature of the soil
Moisture of the soil or water level in the water reservoir
Nutrient or harmful substance content of the soil or of the water in the reservoir
Temperature of the ambient air
Humidity of the ambient air
Lighting current and/or illumination strength of the light incident on the object.

Overall, the above described tasks are solved through the integration of sensors and diverse means for data transmission, data processing and data storage. Since there are different types of plants, there is the necessity of employing different approaches toward a solution. This will be shown in the following using water level measurement as an example.

The present technical problem comprises determining reliably and as invisibly as possible the water level in the pot of a potted plant. This depends on the watering system of the pot. In a sub-irrigation system the plane is supplied with water from below. The pot is conventionally filled with soil and/or clay spheres (swelling clay), the latter absorbing the water. A suitable sensor is depicted in FIGS. 2a to 2d and will be described in the following.

FIGS. 2a to 2d show examples of sensors such as can be utilized in the system according to the invention, and with the aid of which the water column in a sub-irrigation watering system can be measured. These sensor nodes measure the water level and various other physical variables and generate digital output signals which they transfer via radio.

The sensor shown in FIG. 2a is comprised of a housing 20 in which a vertically movable float gauge 21 is disposed which carries a magnet 24 on a rod fixedly connected to it. On the wall opposite the magnet 24 a number of Reed switches 23—in the depicted example four—are disposed such that at different positions of the float 21 different Reed switches are activated. The position of the float 21 depends on the water level such that the Reed switches closed by the magnet 24 directly provide a digital acquisition of the water level. It suffices, for example, to provide one Reed switch for every cm of water level height wherein this also depends on the length and field strength of the utilized magnet 24. It is understood that the number of Reed switches depends also on the difference between minimum and maximum water level. Details of the digitization of the water level are described in the following.

Furthermore, on or in the sensor depicted in FIG. 2a is a battery 25 for the power supply and electronic circuitry 22 which serves for processing or digitizing the determined parameter value(s) and for preparing a data set transferrable via radio. This data set is sent via an antenna 27.

The following sensors can, for example, be disposed additionally in or on the water level indicator: a light sensor 26, an air humidity sensor 28, a temperature sensor 29, wherein these three are preferably located in the upper region of the water level indicator. Moreover, on the bottom or in the lower region a nutrient or harmful substance sensor 30 can be disposed, which acquires the concentration of the nutrient or harmful substances in the pot. To guard against shadowing, the light sensor can optionally be expanded by fiber optics 70. This can be conducted to the upper region of the plant in order to measure here a portion of the microclimate.

Figure 2B:
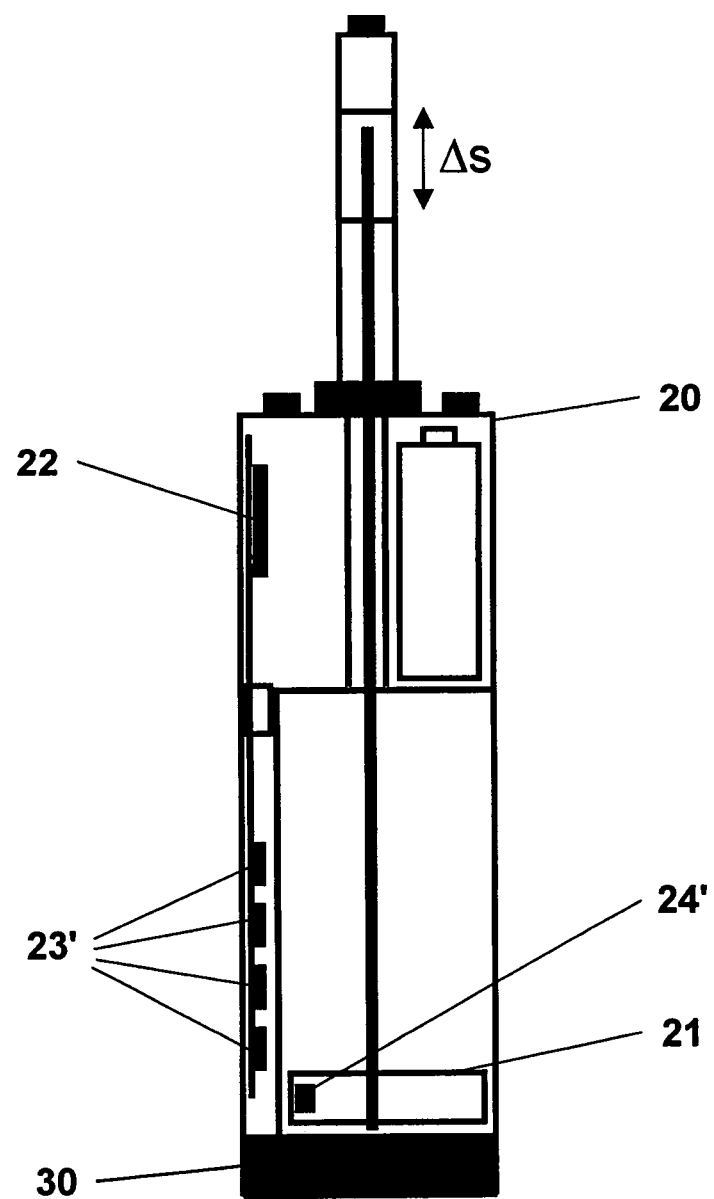

Since the water level indicator depicted in FIG. 2b in principle is comprised of the same parts as the water level indicator in FIG. 2a, the details are therefore not listed here again. In the housing 20, again, the float 21 is disposed wherein here the magnet 24' is located in or on the float 21. On the wall opposite the magnet 24' are located four Reed switches 23' such that at different positions of the float 21 different Reed switches are actuated.

Figure 2C:
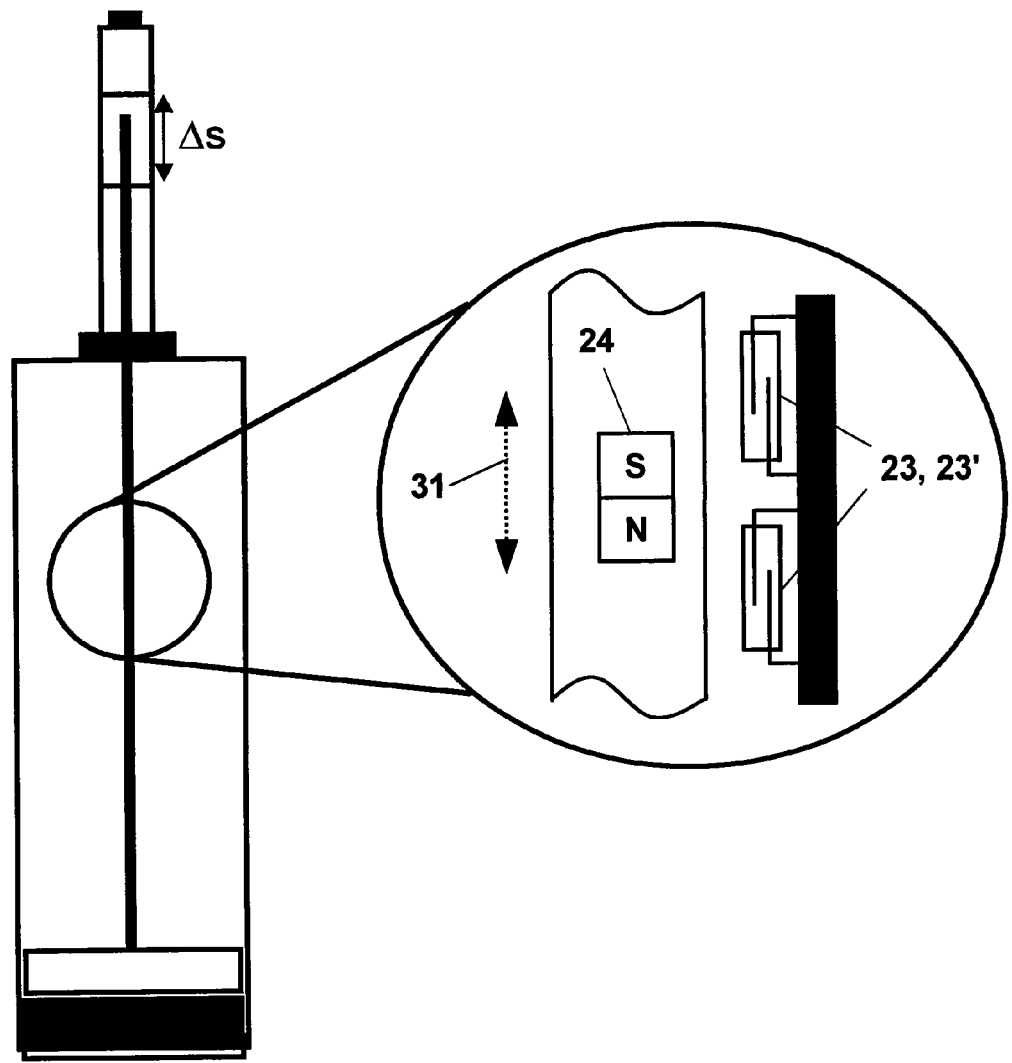

In FIG. 2c the disposition of magnet 24 and Reed switch 23 is once again shown in an enlarged detail wherein this Figure probably does not need further explanation.

It is understood that more than one magnet 24 can be connected to the float 21; in this way the resolution of the configuration, for example, can be improved. In FIG. 2d overall five Reed contacts 23 are shown which are opposite a float with two magnets 24.

This FIG. 2d shows the manner in which the digitized output signal of the water level is generated directly from the positions of the float. In this case a digital signal is directly generated which indicates the water level. In the depicted example two magnets 24 are disposed on the float or are fixedly connected to it, in addition to five Reed switches 23 opposite the magnets; the distances of the Reed switches with respect to each other are less than the distance of the two magnets.

Shown in FIG. 2d are different positions of the magnets 24 from left to right, which correspond to different water levels. In the first depiction or column at the far left the upper magnet is located opposite the uppermost Reed switch such that it closes. In a five-digit binary digital number this corresponds to a first "1" with four following "0". The complete digital number for the upper limit water level is accordingly "10000". If the water level falls, for example due to consumption and evaporation, the float with the magnets 24 moves minimally downwardly and assumes the position depicted in the second column. The uppermost Reed switch remains closed, in addition, the third Reed switch from the top is also closed: the corresponding digital number output is "10100". With the further falling of the water level the digital numbers in the next columns extending toward the right "00100", "01100", etc. are available as indicator of the particular water level. The last column shows the lower limit water level: the associated digital number is "00100".

Figure 2E:
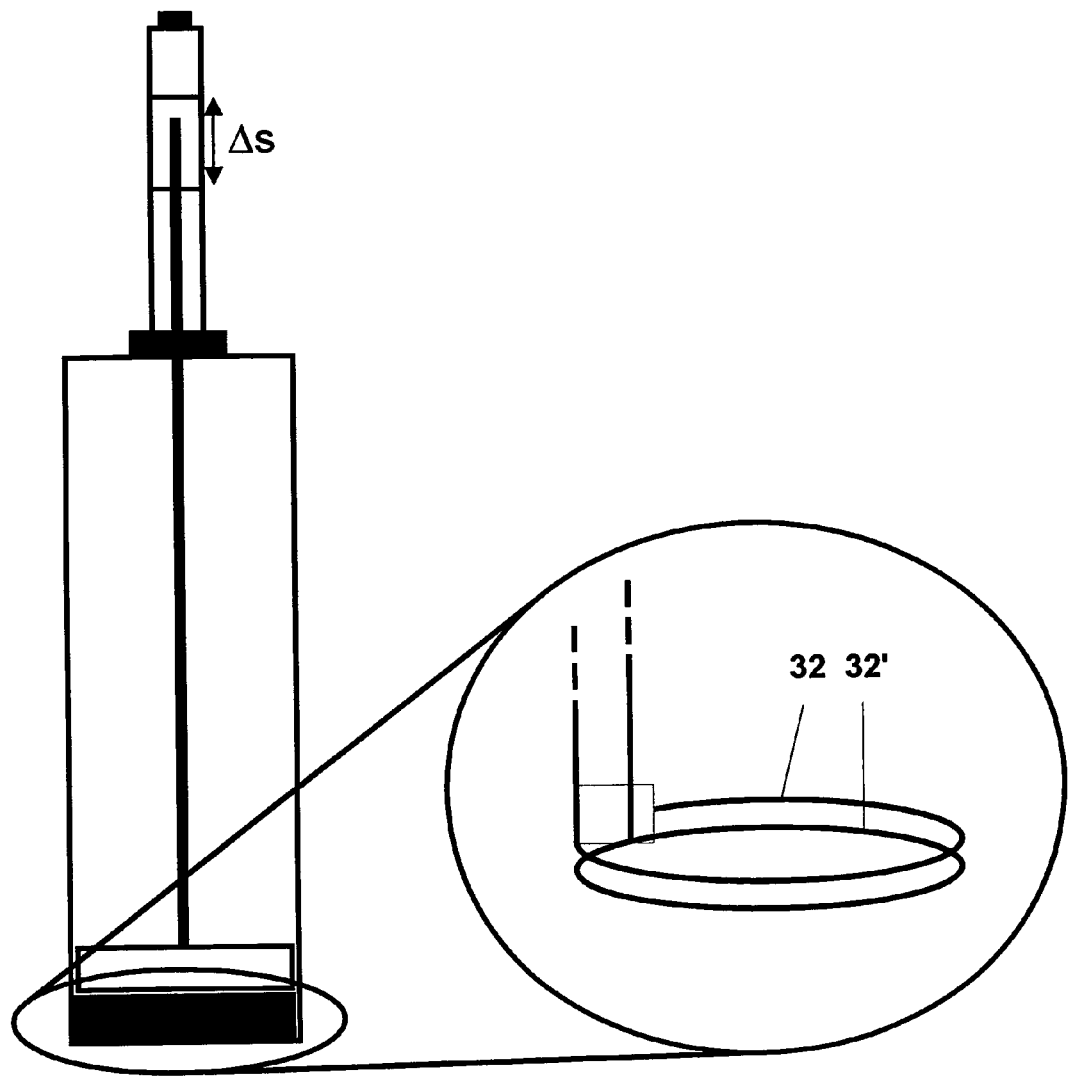

FIG. 2e shows the nutrient or harmful substance sensor 30 in detail. For the nutrient measurement, for example, the conductivity of the water is measured which represents a measure of the salinity, e.g. the salt content, of the water. For this purpose the two measuring electrodes 32 are annularly disposed on the inner margin, e. g. on the inside of the housing 20. In order not to hinder the float 21 from rising or falling, the measuring electrodes 32 are so integrated in the housing that the surface of the housing 20 does not change. A low-corrosion metal or other conductive material can be utilized as electrode material. For this purpose in particular graphite, platinum and titanium are especially to be considered, wherein, for reasons of cost, titanium or a titanium alloy are advantageous for use. In particular titanium grade 2 is suitable for this purpose. For the measurement a current is applied for a short time to the two measuring electrodes 32 and by means of the electronic circuitry 22 the electrical resistance between the measuring electrodes 32 is determined. The inverse of the resistance is denoted as conductivity of water and serves for determining its salinity. In this way the most important inorganic nutrient compounds can be demonstrated, among which are in particular nitrogen and nitrogen-containing compounds, potassium and phosphorus.

The intelligent flower pot can further be utilized as a relay station for the transfer of data or data packets which it receives from other sensors, in particular those having low transmitting power, such as, for example, the so-called sensor clip. This is possible because the flower pot according to FIGS. 5a to 5d, in comparison to the sensor clip of FIG. 3, contains a relatively powerful power supply. A corresponding example of a sensor clip with weak power supply will be described in the following.

In FIG. 3 is depicted another sensor node shaped in the form of a leaf, a fruit or a blossom, which in the following will be referred to as sensor clip. This sensor clip also comprises several sensors suitable for measuring, for example temperature and humidity of the air surrounding the plant, e.g. its microclimate. Moreover, a light-sensitive sensor disposed on the sensor clip serves for measuring the incident light, and by which its time distribution can also be determined.

The sensor clip in FIG. 3 is a simplified variant of a sensor node to the extent that it is laid out for especially low power consumption. It becomes therefore possible to operate it by means of a solar cell which makes a battery superfluous or possibly only a small buffer battery is necessary. However, the desired low power consumption results in a shorter range when transmitting the determined data. The transfer of received data packets such as can be carried out by other sensor nodes is thus eliminated.

The sensor clip should, moreover, be of low weight in order for it to be disposed in simple manner on or in the proximity of the plant, for example inconspicuously on its stem without affecting the overall impression.

The sensor clip 33 depicted schematically in FIG. 3 in the form of a leaf is comprised of a support 35, for example, a synthetic material film, which can simultaneously be implemented as a solar cell. On the "stem" is located a securement part 38 with which the sensor clip 33 can be attached to the plant itself or to a holder. The solar cell on the surface of the sensor clip serves as the power supply. Also disposed on the surface in the depicted sensor clip are a total of three sensors 34. These measure the incident light, the temperature and the humidity of the ambient air. The sensors and the solar cell are connected to electronic circuitry 36 which is virtually invisibly disposed on the underside of the leaf. This electronic circuitry 36 assumes the analysis of the values determined by the sensors and the transfer of the digital parameter signals obtained therefrom by means of a transmitter via the antenna 37 to the gateway 6 or, in the case of a relay station, initially to the intelligent flower pot, wherein here, as a rule, only short distances of 1-2 meters must be overcome.

Suitable dispositions of such a sensor clip are shown in FIGS. 4a and 4b. In both cases the sensor clip 44 is fastened on a rod 43 which is inserted next to the plant 42 in the soil of the flower pot 41. In FIG. 4a the sensor clip 44 is implemented as a leaf as shown in FIG. 3. In FIG. 4b the sensor clip 44 is implemented as a blossom and thus also relatively inconspicuous next to the plant.

There are also plants whose leaves must be moistened regularly. On such a plant a sensor clip disposed on a leaf can serve for detecting the process of spraying or even to offer the advice that the plant needs to be sprayed with water.

In the case of a surface watering system in which the water supply is provided from above, a sensor according to FIG. 2a or 2b cannot be utilized. In such a system the entire pot is conventionally filled with soil, which does not allow the soil moisture to be determined via the water level. Added to this is the fact that a sensor introduced from above into the soil measures too imprecisely since, on the one hand, the water collects in the lower region and can here even lead to the rotting of the plant, on the other hand, the soil dries from the top down. There are several approaches to a solution for this case.

As the solution described in prior art proposes, it is feasible to utilize a moisture sensor introduced from above into the soil in order to measure the moisture of the soil. However, since the soil dries out from the top to the bottom, the moisture at the surface is only marginally significant and thus such a measurement highly imprecise.

An entirely different approach consists in measuring the moisture according to the invention in the soil in the flower pot at several locations, potentially also at different heights, and disposing further sensors in or on the pot for determining additional parameters. Stated differently, no sensor is disposed on or in a conventional flower pot but rather the pot itself is equipped inside and/or outside with several sensors which supply corresponding data. Such an "intelligent flower pot" is shown in FIGS. 5a to 5d in several different embodiments and will be described in the following in further detail.

FIG. 5a shows a first embodiment example of such an intelligent flower pot in cross section which corresponds to a surface watering system. FIGS. 5b and 5c show a second, modified embodiment example which corresponds to a sub-irrigation watering system. FIG. 5e, lastly, shows a top view onto the flower pot.

The pot 50 in FIG. 5a is filled up to level 51 with soil, swelling clay or an hors-sol material. On the upper edge, the margin of the pot 50, is disposed at least one light-sensitive sensor, light sensor 52. Several such light sensors can also be distributed over the edge of the pot 50. In the pot, furthermore, are located a number of rod-shaped electrodes 56, which, starting from the bottom of the pot, extend into the soil. These serve as soil moisture sensors. The more electrodes disposed in the pot, the more precise is the measurement since it is possible to differentiate between different regions of the pot. In FIG. 5a the electrodes are shown to be of unequal lengths, however, they can also be of like length. The advantage of this disposition is that the soil moisture is, in fact, determined in the proximity of the roots of the plant and not at the frequently dried out soil surface. The electrodes themselves measure the electrical capacitance which is a measure of the so-called dielectric value which is a degree of relative permittivity. This value can in particular be determined through a frequency measurement.

Furthermore at the bottom of the pot 50 a temperature sensor 53 is provided for the measurement of the temperature obtaining here.

Within the soil also at the bottom of the pot 50 is located a nutrient sensor 55 which determines the nutrient or harmful substance content of the soil.

Insulated and sealed off, electronic circuitry 58 is embedded in the bottom of the pot 50. It serves for processing, in particular digitizing, the data determined by the sensors and prepares the data packets intended for the wireless transfer. The transfer takes place via the antenna 59 which is located on the outer wall of the pot 50.

Power is supplied from a battery 60 which is also, insulated and sealed-off, embedded in the bottom of the pot 50, however, in such manner that it can be replaced without having to empty the pot. A supply from an external power source, in particular a wall socket, is also feasible.

The modified pot 50 in FIG. 5b is also filled up to level 51 with soil. On the upper edge, the margin of the pot 50, are disposed two light-sensitive sensors, light sensor 52 and 52'. It is understood that here also several such light sensors can be distributed over the edge of the pot 50.

Furthermore, above the level 51 of the soil in the pot 50 a moisture sensor 54 is disposed which determines the air humidity in the pot in the proximity of the soil surface.

In the upper region of the pot 50, however below the level 51 are located two nutrient sensors 55 and 55' which monitor the nutrient content of the soil in the pot. A third nutrient sensor 55", which can be implemented as a nitrogen sensor for example, is located at the bottom of the pot within the soil.

In addition, at the bottom of the pot 50 again two rod-shaped electrodes are disposed which function as soil moisture sensor 56. They project into the soil and determine the moisture of the soil in the pot.

Insulated against the soil and embedded in the bottom of the pot 50 is circuitry 58. This circuitry has several functions. On the one hand, it is connected to all sensors that are disposed on and in the pot 50 and processes, in particular digitizes, the parameter values received from these sensors, and on the other hand, it supplies the digitized data for the wireless transfer to the central server SOS 6.

This wireless transfer takes place via an antenna 59 which is located at the upper edge of the pot 50. A second antenna 59' can be disposed laterally on pot 50 and can potentially be operated optionally or additionally. These antennae serve mainly for transferring the digitized data determined by the various sensors in and on the pot.

If the plant, not shown in FIGS. 5a and 5b, in the pot 50 carries one of the sensor clips 44 described in connection with FIGS. 4a and 4b or such sensor clip is disposed in the pot 50, one of the provided antennae can also be utilized for the reception of the data transferred from the sensor clip 44. Processing these sensor clip data subsequently also takes place in the circuitry 58 which, in this case, serves as a relay station.

The energy required for the operation of the circuitry 58 and the transfer, and possibly of the sensors, is supplied by a battery 60, which is housed in a compartment of the pot accessible from the outside such that it is insulated against the soil in the pot 50 and can be readily replaced.

FIG. 5c [sic: 5e] shows a top view onto an, again, minimally modified smart flower pot. Two light sensors 52 and 52' are here placed on the upper edge of the pot, in addition, two RFID tags 61 and 61' and two nutrient sensors 55 and 55' on the inner wall of the pot. On the bottom thereof two electrodes 56 for the soil moisture sensor and one nitrogen sensor 57 are located.

FIGS. 5c and 5d show a further embodiment of the smart flower pot, this time suitable for plants that are supplied with water through sub-irrigation watering. The water level sensor 20 is connected across electronic circuitry to the smart flower pot 50 such that it forms a unit. The water level sensor 20 is connected across a connection 63 in such a way with the interior of the pot 50 that water can reach the water level sensor 20. FIG. 5d shows the intelligent flower pot without the water level sensor 20. The problem of water level measurement is here solved through electrodes 67, which, for example, can measure the water level through resistance measurement or via capacitance measurement.

Two further embodiment examples are shown in FIGS. 6a and 6b. In both, said water level sensor 20 and a moisture sensor 68 are electrically combined to form a unit. This solution is reasonable, for example for a transition time if the owner does not wish to repot his plant into the above described intelligent flower pot but rather wishes to leave it in its current pot system. Here there are two configuration feasibilities. As shown in FIG. 6a the circuitry 22, the battery 25 as well as the necessary radio module, which preferably is part of the circuitry 22, can be located in the water level sensor 20. However, usually the problem is encountered that batteries in particular require much space and therefore can only with difficulty be accommodated in the outer wall of the water level indicator.

In a second configuration depicted in FIG. 6b, the circuitry 22, the battery 25 as well as the necessary radio module are located in the moisture sensor 68. In the case of this sensor space problems are rarely encountered such that a greater and therefore more cost-effective battery can be utilized. Moreover, in this configuration the battery is located in the "dry region" outside of the pot which can often be advantageous. In both configurations the water level and the moisture sensor are connected to one another across a cable 69. This cable can be, for example, a USB cable. This cable serves for exchanging data between the two sensors as well as to supply them with energy. Data flow across the cable from a sensor to the circuitry 22 of the other sensor. The power supply from the battery 25 is also possible in this manner.

It will not present a problem to the person of skill in the art to develop and produce a smart flower pot which fulfills specific conditions and requirements regardless of whether they originate from the plant or the end user or owner.

The invention claimed is:

1. A system for determining a state or a state change of a potted plant and for indicating said state or state change to a user by wireless communication, comprising
    a mobile, self-powered sensor clip or sensor unit mountable on or close to said plant, said sensor clip or sensor unit including
    a power supply,
    placed on or within a culture medium in a pot or other vessel at least two cross-linked sensors, each said sensor determining at least one physical and/or chemical parameter, each said parameter being represented as an electrical parameter signal,
    placed on or within said pot or in one of said sensors an electronic device which transforms each said electrical parameter signal into a digitally encoded parameter signal,
    a wireless transmitter for transmitting each said digitally encoded parameter signal in realtime to a receiver located outside said pot or other vessel,
    at least one of said at least two cross-linked sensors determining the contents of nutritive and/or harmful substances within said culture medium.

2. The system according to claim 1, wherein
    the sensor or sensors determining the contents of nutritive and/or harmful substances within the culture medium identifies the conductivity of the culture medium or of a groundwater in the pot or vessel, by measuring the resistance between two accordingly placed electrodes.

3. The system according to claim 1, further comprising
    at least one of the at least two cross-linked sensors equipped for measuring at least one of the following physical or chemical parameters:
    temperature and/or moisture of said culture medium,
    temperature and/or humidity of the ambient atmosphere, and/or
    duration and/or intensity and/or nature of light or other radiation to which the plant is exposed.

4. The system according to claim 1, wherein
    the digitally coded parameter signals are transmitted wireless via an existing communication network.

5. The system according to claim 1, including
    a plurality of the at least two cross-linked sensors for determining the moisture within the culture medium and/or the contents of nutritive and/or harmful substances therein, said sensors being placed in differing levels of the pot or vessel.

6. The system according to claim 1, including
    a plurality of the at least two cross-linked sensors for determining the moisture within the culture medium and/or the contents of nutritive and/or harmful substances therein, said sensors extending from the bottom of the pot or vessel and having different lengths.

7. The system according to claim 1, wherein at least one of the at least two cross-linked sensors is configured as a movable float gauge for determining the moisture within the culture medium by identifying a level of a liquid within said culture medium.

8. The system according to claim 1, further including an RFID tag attached to the pot or vessel for identifying said pot or vessel by an RFID reader.

9. The system according to claim 1, wherein the mobile sensor clip has a plant-like structure, in particular approximately the form of a leaf, a fruit, a blossom, or a flower, whereby a part of said structure is configured as or includes a solar cell for said clip's power supply.

10. The system according to claim 1, wherein a plurality of more than two of the at least two cross-linked sensors is provided, at least two of which are connected by wire whereas the remaining sensors are wireless cross-linked.

11. The system according to claim 1, wherein at least one of the at least two cross-linked sensors generates digitally encoded parameter signals and/or includes a transmitter for transmitting said digitally encoded parameter signals.

12. The system according to claim 1, wherein at least one of the at least two cross-linked sensors is placed at the upper end or rim of the pot or vessel for determining duration and/or intensity and/or nature of the light or other radiation to which the plant is exposed.

13. The system according to claim 12, wherein at least one of the at least two cross-linked sensors comprises a plurality of locally distributed sensors.

14. The system according to claim 1, wherein the digitally encoded parameter signals are transmitted wireless via an existing WLAN and/or the Internet.

15. The system according to claim 1, wherein the at least two cross-linked sensors are placed at a wall of the pot or vessel.

16. A method for operating a monitoring system for determining a state or a change of state of a potted plant and for indicating said state or change of state to a user by wireless communication, comprising the steps of:
mounting a mobile, self-powered sensor clip or sensor unit on or close to said plant, said sensor clip or sensor unit including a power supply,
placing on or within a culture medium in a pot or other vessel at least two cross-linked sensors, each said sensor for determining at least one physical and/or chemical parameter, each said parameter being represented as an electrical parameter signal,
placing on or within said pot or in one of said sensors an electronic device for transforming each said electrical parameter signal into a digitally encoded parameter signal, and a wireless transmitter for transmitting each said digitally encoded parameter signal in realtime to a receiver located outside said pot or other vessel,
deriving, from said at least two cross-linked sensors, at least two physical and/or chemical parameters, one of them indicating the contents of nutritive and/or harmful substances within said culture medium in said pot or vessel containing said potted plant,
representing each said physical and/or chemical parameter as an electrical parameter signal,
transforming, by said electronic device, said representative electrical parameter signal into a digitally encoded parameter signal,
transmitting, by said wireless transmitter, said digitally encoded parameter signal in real-time to a receiver located outside said pot or vessel,
processing said digitally encoded parameter signals received in said receiver and deriving output signals representing the state or change of state of said plant,
transmitting said output signals wirelessly to an indicating or display device of the user of said plant, and
displaying or otherwise indicating to said user the state or change of state of said plant.

17. The method according to claim 16, wherein a further parameter of the at least two physical and/or chemical parameters is one of the group of:
temperature and/or moisture of the culture medium, and/or
temperature and/or humidity of an ambient atmosphere, and/or
duration and/or intensity and/or nature of light or other radiation to which the plant is exposed.

18. The method according to claim 16, wherein the physical and/or chemical parameters are determined in real-time and the digitally coded parameter signals derived therefrom are transmitted to the user without delay.

19. The method according to claim 16, wherein the user is alarmed whenever any of the digitally coded parameter signals or any therefrom derived output signals concerning a plant of said user indicates a dangerous state of said plant.

20. The method according to claim 19, wherein the user is alarmed in realtime.

\* \* \* \* \*